United States Patent [19]
Yoshioka et al.

[11] Patent Number: 5,192,415
[45] Date of Patent: Mar. 9, 1993

[54] BIOSENSOR UTILIZING ENZYME AND A METHOD FOR PRODUCING THE SAME

[75] Inventors: Toshihiko Yoshioka, Osaka; Shiro Nankai, Hirakata, both of Japan

[73] Assignee: Matsushita Electric Industrial Co., Ltd., Osaka, Japan

[21] Appl. No.: 845,073

[22] Filed: Mar. 2, 1992

[30] Foreign Application Priority Data

| Mar. 4, 1991 | [JP] | Japan | 3-37259 |
| Mar. 4, 1991 | [JP] | Japan | 3-37261 |
| Sep. 2, 1991 | [JP] | Japan | 3-221402 |
| Jan. 14, 1992 | [JP] | Japan | 4-04592 |

[51] Int. Cl.$^5$ .............................................. G01N 27/26
[52] U.S. Cl. .................................. 204/403; 204/412; 204/416; 204/153.12
[58] Field of Search ............. 204/403, 412, 416, 153.12

[56] References Cited

U.S. PATENT DOCUMENTS

4,897,173  1/1990  Nankai et al. .................. 204/403
5,120,420  6/1992  Nankai et al. .................. 204/403

FOREIGN PATENT DOCUMENTS

0359831  3/1990  European Pat. Off.
0400918  12/1990  European Pat. Off.
1114747  5/1989  Japan.
9109139  6/1991  PCT Int'l Appl.

*Primary Examiner*—John Niebling
*Assistant Examiner*—Bruce F. Bell
*Attorney, Agent, or Firm*—Panitch, Schwarze, Jacobs & Nadel

[57] ABSTRACT

The biosensor of the present invention quantifies a substrate contained in a sample liquid by reducing electron acceptors using electron generated in a reaction of the substrate to enzyme and then by measuring the reduced amount of the electron acceptors electrochemically. The biosensor has an electrical insulating substrate, an electrode system including at least a working electrode and a counter electrode, a reaction layer including the enzyme provided on the electrode system and a hydrogen ion concentration control layer, and the reaction layer is in contact with the electrode system. According to the present invention, the hydrogen ion concentration in the sample liquid can be made most appropriate in accordance with the type of the enzyme contained in the reaction layer, without the adjustment of the hydrogen ion concentration in the sample liquid beforehand. Thus, the specific substrate contained in the sample liquid can be easily quantified with accuracy and speed.

13 Claims, 7 Drawing Sheets

BIOSENSOR UTILIZING ENZYME AND A METHOD FOR PRODUCING THE SAME

BACKGROUND OF THE INVENTION

1. Field of the Invention

The present invention relates to a biosensor that can easily quantify a specific component in a sample liquid with accuracy and speed, and a method for producing the same, and more particularly to a biosensor for quantifying a specific component in a sample liquid by reducing electron acceptors using electrons generated in the reaction of the specific component in the sample liquid to enzyme that specifically reacts to the component, and then by electrochemically measuring the reduced amount of electron acceptors, and a method for producing the same.

2. Description of the Prior Art

Various types of biosensors utilizing specific catalyses of enzyme have been recently developed. A saccharide biosensor will be described as an example of such biosensors as follows:

The optical rotation method, the colorimetric method, the reductimetry method and other methods using different kinds of chromatographies have been developed as method for quantitative analysis of saccharides. However, none of these methods can provide high accuracy due to the relatively low specificity against saccharides. Additionally, the optical rotation method is easy to operate but is largely influenced by the operating temperature. Therefore, it is not appropriate for common use at home and the like.

The saccharides contained in fruit are generally assessed as saccharine degrees. A refractometer of the light refraction system is often used for quantifying the saccharine degree. This refractometer functions by utilizing change of the light refractive index caused by liquid concentration. Therefore, the refractometer of the light refraction system is influenced by all the components dissolved in the sample liquid, for example, by organic acid such as citric acid or malic acid contained in fruit juice in a large amount when a saccharide in fruit is quantified. Thus, accurate quantification by this refractometer is impossible.

A glucose sensor will now be described as an example of a biosensor used in a clinical field.

A conventional method for quantifiying glucose contained in blood is to centrifuge blood taken from a patient and then to measure the thus obtained blood plasma. This method requires a lot of time as well as labor. Therefore, a sensor that can directly measure glucose in blood obtained from a patient has been desired.

A sensor similar to a test paper for urinalysis has been developed as a simple glucose sensor. This glucose sensor comprises a support in a stick shape and a holder fixed to the support. The holder includes an enzyme reacting only to glucose and a dye the color of which is changed by reacting with a production of the enzyme reaction. Blood is dropped on the support of the glucose sensor and the change of the dye after a predetermined period of time of the dropping is visually observed or optically measured, whereby the content of glucose in the blood can be measured. However, the quantifying method using this glucose sensor has low accuracy due to the interference by the colored materials in the blood.

Figure 7:
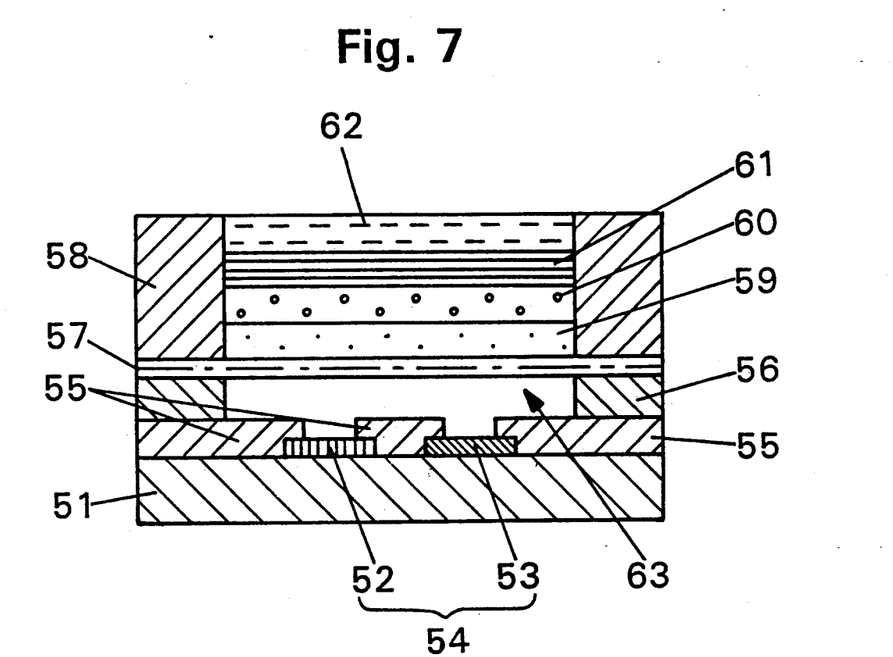
FIG. 7 is a diagram showing an example of a conventional biosensor.

Japanese Laid-Open Patent Publication No. 1-114747 discloses the following glucose sensor with high accuracy as a method for quantifying a specific component in a sample liquid from a living body such as blood without diluting or stirring the sample liquid:

As shown in FIG. 7 this glucose sensor comprises an electrical insulating substrate 51, an electrode system 54 including a working electrode 52 and a counter electrode 53 formed on the insulating substrate 51 by screen printing, an electrical insulating layer 55 formed on the insulating substrate 51, an adhesive structure 56 provided on the electrical insulating layer 55, a filtration layer 57 supported by the adhesive structure 56, a holding frame 58 provided on the filtration layer 57, and an electron acceptor holding layer 59, an enzyme holding layer 60, a buffering salt holding layer 61 and an expansion layer 62 which are supported by the holding frame 58. A space 63 for containing a sample liquid is formed between the electrode system 54 and the filtration layer 57.

The filtration layer 57 is made from a porous polycarbonate film. The electron acceptor holding layer 59, the enzyme holding layer 60 and the buffering salt holding layer 61 use porous cellulose as supports.

The operation of such a glucose sensor is as follows: The sample liquid dropped on the expansion layer 62 is adjusted to pH that provides the most stable enzyme activity by the action of the buffering salt in the buffering salt holding layer 61. Then, in the enzyme holding layer 60, the glucose oxidase in the enzyme holding layer 60 and the glucose in the sample liquid specifically react to each other. The potassium ferricyanide in the electron acceptor holding layer 59 is then reduced to become potassium ferrocyanide by electrons generated in the above reaction. The amount of the potassium ferrocyanide generated at this time is in proportion to the glucose concentration in the sample liquid. Next, materials with larger molecular weight such as protein are filtered in the filtration layer 57, and the filtered liquid drops in the space 63 above the electrode system 54. Thus the amount of potassium ferrocyanide in the liquid can be measured by measuring the oxidation current of the liquid by the electrode system 54, thereby measuring the glucose concentration.

In the conventional glucose sensor with the above-mentioned structure, frothing may remain in the space due to the inconstant flow of the liquid in the space 63, which influences the measured value of the glucose concentration.

Furthermore, since the buffering salt holding layer 61 is in contact with the enzyme holding layer 60, the buffering salt and the enzyme are mixed on the interface between the two layers when the glucose sensor absorbed moisture, thereby deteriorating the enzyme activity by the chemical interaction. As a result, the glucose sensor of this type is hard to store in a stable condition.

Moreover, since insoluble porous materials are used as supports of the filtration layer 57 and each of the holding layers 59, 60, and 61 in the conventional glucose sensor, the sample liquid supplied to the glucose sensor is required to pass through each of the porous materials before reaching the electrode system 54. Therefore, the sensor has disadvantages that it may take longer time to obtain the reaction and/or that the response values may be variable due to the variable reaction time. Additionally, the glucose sensor has so many steps in its production, including such a complicated step as to assemble a plurality of porous materials, that it is difficult to produce it at a low cost.

SUMMARY OF THE INVENTION

The biosensor of this invention for quantifying a substrate contained in a sample liquid by reducing electron acceptors using electrons generated in a reaction of the substrate to enzyme and then by measuring the reduced amount of the electron acceptors electrochemically, which overcomes the above-discussed and numerous other disadvantages and deficiencies of the prior art, comprises an electrical insulating substrate, an electrode system including at least a working electrode and a counter electrode which are formed on the insulating substrate, a reaction layer including the enzyme provided on the electrode system, and a hydrogen ion concentration control layer, wherein the reaction layer is in contact with the electrode system.

In a preferred embodiment, the reaction layer further includes hydrophilic polymer and electron acceptors.

In a preferred embodiment, the reaction layer further includes hydrophilic polymer and the hydrogen ion concentration control layer includes electron acceptors.

In a preferred embodiment, the reaction layer is formed by laminating a first layer including hydrophilic polymer and enzyme, a second layer including hydrophilic polymer and a third layer including electron acceptors in this order.

In a preferred embodiment, the hydrogen ion concentration control layer is provided on the electrode system.

In a preferred embodiment, the reaction layer further includes hydrophilic polymer and electron acceptors, and a hydrophilic polymer layer is provided between the reaction layer and the hydrogen ion concentration control layer.

In a preferred embodiment, the reaction layer comprises a first layer including hydrophilic polymer and electron acceptors and a second layer including enzyme laminated on the first layer, and the hydrogen ion concentration control layer is provided on the second layer.

In a preferred embodiment, the electrode system is mainly formed from carbon.

In a preferred embodiment, the hydrogen ion concentration control layer includes buffering salt selected from a group consisting of potassium biphosphate-dipotassium phosphate, potassium biphosphate-disodium phosphate, citric acid-disodium phosphate, citric acid-trisodium citrate, potassium bicitrate-sodium hydroxide and maleic acid monosodium salt-sodium hydroxide.

In a preferred embodiment, the hydrophilic polymer is selected from a group consisting of polyvinyl alcohol and cellulose derivatives, specifically, hydroxy propyl cellulose, methyl cellulose, ethyl cellulose, ethyl hydroxyethyl cellulose and carboxy methyl ethyl cellulose, polyvinylpyrrolidone, gelatin or its derivatives, (meth)acrylic acid or its salts, starch or its derivatives and maleic anhydride or its salts.

In a preferred embodiment, the enzyme is selected from a group consisting of fructose dehydrogenase, invertase, mutarotese, glucose oxidase, alcohol oxidase, lactase oxidase, lactase dehydrogenase, cholesterol oxidase, xanthine oxidase and amino acid oxidase.

In a preferred embodiment, the electron acceptor is selected from a group consisting of potassium ferricyanide, p-benzoquinone, phenazinemethosulfate and ferrocene.

Alternately, the present invention provides a method for producing a biosensor for quantifying a substrate contained in a sample liquid by reducing electron acceptors using electrons generated in a reaction of the substrate to enzyme and then by measuring the reduced amount of the electron acceptors electrochemically, the method comprising the steps of:
firstly, providing an electrode system including at least a working electrode and a counter electrode on an electrical insulating substrate;
secondly, forming a hydrogen ion concentration control layer including electron acceptors on the insulating substrate; and
finally, forming a reaction layer including hydrophilic polymer and enzyme on the electrode system.

Thus, the invention described herein makes possible the objectives of providing (1) a biosensor in which the hydrogen ion concentration of a sample liquid can be made most adequate in accordance with the type of enzyme contained in a reaction layer without prior adjustment of the hydrogen ion concentration in the sample liquid, (2) a biosensor which can easily quantify a specific substrate contained in a sample liquid with accuracy and speed, (3) a biosensor in which the reliability in performance thereof while being stored can be improved by separating buffering salt contained in a hydrogen ion concentration control layer from enzyme contained in a reaction layer by a hydrophilic polymer layer, (4) a method for producing a biosensor in a short period of time by heating layers such as a hydrogen ion concentration control layer including electron acceptors, and (5) a method for producing a biosensor, in which crystal diameters of electron acceptors contained in a layer can be optionally controlled by controlling the temperature in heating the layer.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

A biosensor according to the present invention comprises an electrical insulating substrate, an electrode system including a working electrode and a counter electrode provided on the insulating substrate, a reaction layer including enzyme provided on the electrode system and a hydrogen ion concentration control layer provided on the insulating substrate.

According to the present invention, the enzyme is not influenced by the buffering salt included in the hydrogen ion concentration control layer because the reaction layer including the enzyme is formed separately from the hydrogen ion concentration control layer. Therefore, the contained enzyme can be kept in a stable condition when the biosensor is stored.

Generally, the pH of a sample liquid is not necessarily the same as that of the specified enzyme in the reaction layer that provides the highest enzyme activity. In accordance with the present invention, the pH of the sample liquid can approximate to the value which provides the highest activity of the enzyme by allowing the sample liquid supplied to the sensor to reach the hydrogen ion concentration control layer. As a result, the sensor can be simply operated because there is no need to adjust the pH of the sample liquid by a buffer solution or the like.

A method for producing a biosensor of the present invention comprises steps of providing an electrode system including at least a working electrode and a counter electrode on an electrical insulating substrate, forming a hydrogen ion concentration control layer including at least electron acceptors, and finally forming a reaction layer including at least hydrophilic polymer and enzyme on the electrode system.

Generally the activity of enzyme is largely reduced in a treatment at a temperature of several tens of degrees centigrade. According to the method of the present invention, the reaction layer is not treated at a high temperature that may inhibit the enzyme activity, since the hydrogen ion concentration control layer including the electron acceptors is formed prior to the formation of the reaction layer including the enzyme. Therefore, it is possible to set the heat treatment condition of the hydrogen ion concentration control layer optionally depending upon the objectives of the biosensors. For example, the particle diameter of the crystal of the electron acceptor of the drying condition thereof can be controlled so as to be most appropriate, by making shorter the heating time of the hydrogen ion concentration control layer and/or by controlling the heating temperature of the hydrogen ion concentration control layer.

The use of the biosensor of the present invention depends upon the substrate (the specified component), that is, the object to be measured, contained in the sample liquid. The sensor may be used as, for example, a fructose sensor, a sucrose sensor, a glucose sensor, an alcohol sensor, a lactic acid sensor, a cholesterol sensor and an amino acid sensor.

The enzyme used in the present invention depends upon the substrate contained in the sample liquid and is not limited. The usable enzyme are, for example, fructose dehydrogenase, invertase, mutarotase, glucose oxidase, alcohol oxidase, lactase oxidase, lactase dehydrogenase, cholesterol oxidase, xanthine oxidase and amino acid oxidase.

Any buffer solution with pH that provides the highest activity of enzyme used for producing a biosensor may be chosen in order to form the hydrogen ion concentration control layer. The usable buffer solutions are, for example, a phosphate buffer solution, a McIlvaine buffer solution, citric acid-trisodium citrate, potassium bicitrate-sodium hydroxide and maleic acid monosodium salt-sodium hydroxide. Further, a buffer solution which is liquid at an ordinary temperature such as an acetic acid-sodium acetate buffer solution may be used. In this case, the hydrogen ion concentration control layer may be formed together with a polymer with a long shelf life.

The hydrophilic polymer used in this invention is not limited. The usable hydrophilic polymers are, for example, polyvinyl alcohol and cellulose derivatives. Specifically, hydroxy propy cellulose, methyl cellulose, ethyl cellulose, ethyl hydroxyethyl cellulose and carboxy methyl ethyl cellulose, polyvinylpyrrolidone, gelatin or its derivatives, (meth)acrylic acid or its salts, starch or its derivatives and maleic anhydride or its salts.

As for the electron acceptors in this invention, potassium ferricyanide, p-benzoquinone, phenazinemethosulfate and ferroucene may be used.

The above-described electrode system is not limited to a two-electrode system having only a working electrode and a counter electrode. For example, a three-electrode system, including an additional reference electrode, may be used, so that more precise values are obtainable.

EXAMPLES

Throughout the drawings mentioned in the following description of the examples, the same element has a common reference numeral. Part of the description of the producing procedure is omitted as occasion demands.

EXAMPLE 1

A fructose sensor will now be described as an example of a biosensor.

Figure 1:
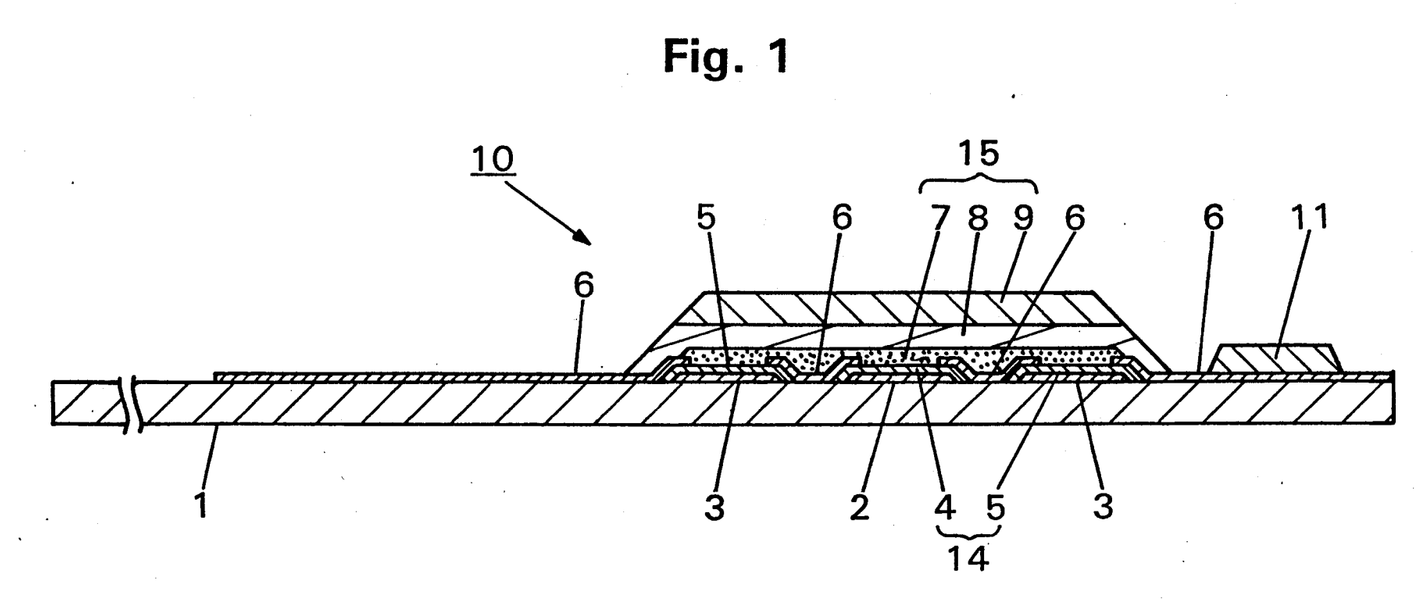
FIG. 1 is a sectional view of a base of a fructose sensor according to an example of a biosensor of the present invention.
Figure 2:
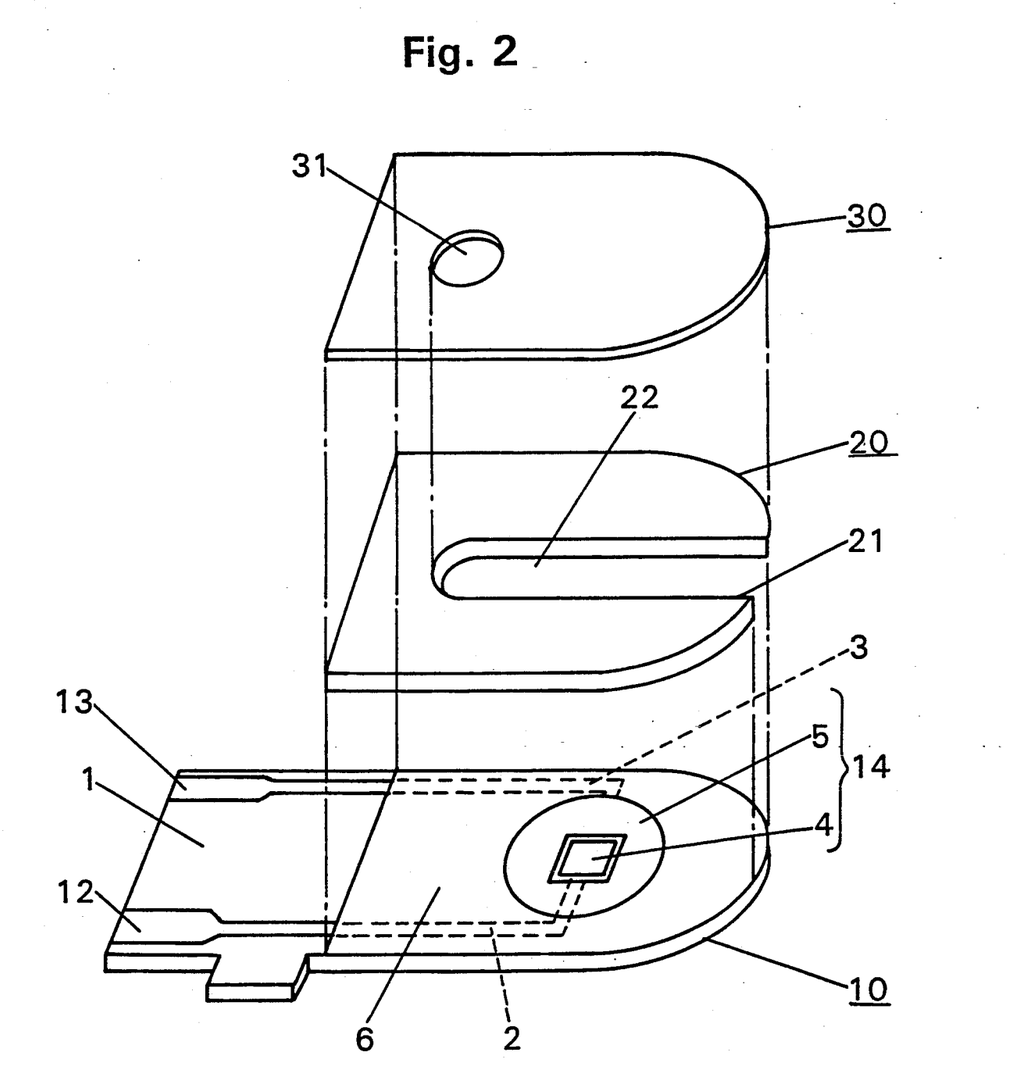
FIGS. 2 and 3 are exploded perspective views of the fructose sensor of FIG. 1.
Figure 3:
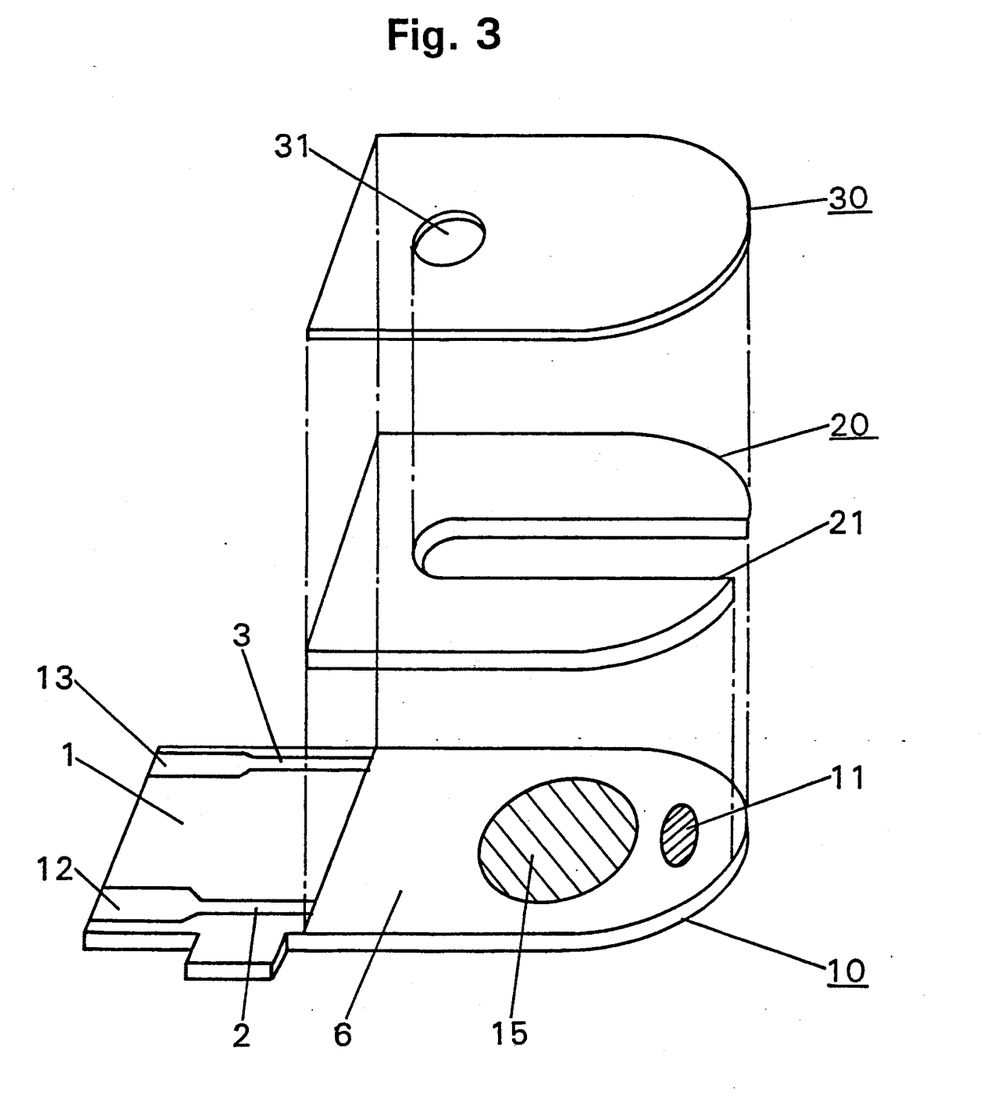

A fructose sensor of the present invention comprises a base 10, a spacer 20 adhered to the base 10 and a cover 30 adhered to the spacer 20 as shown in FIGS. 1 to 3. FIG. 1 shows a sectional view of the base 10 of the fructose sensor, and FIG. 2 shows an exploded perspective view of the fructose sensor with a reaction layer 15 and a hydrogen ion concentration control layer 11 removed from the base 10. FIG. 3 is also an exploded perspective view of the fructose sensor.

Silver paste was printed by means of screen printing on an electrical insulating substrate 1 made from polyethylene terephthalate to form leads 2 and 3. Then, an electrode system 14 (a working electrode 4 and a counter electrode 5) made from conductive carbon paste including resin binder and an insulating layer 6 made from insulating paste were formed by screen printing. The insulating layer 6 was covering the leads 2 and 3 except for connecting portions 12 and 13 with a connector so that the predetermined areas of the working electrode 4 and the counter electrode 5 were exposed respectively.

Then, the exposed portions of the working electrode 4 and the counter electrode 5 were ground and heat treated for 4 hours at 100° C. in the air.

After forming the electrode system 14 comprising the working electrode 4 and the counter electrode 5 in this way, an aqueous solution including 0.5 wt % of carboxymethyl cellulose (hereinafter called the CMC), as hydrophilic polymer, was dropped on the electrode system 14 and dried, to form a CMC layer. Then an aqueous solution of fructose dehydrogenase (manufactured by Toyo Boseki Kabushiki Kaisha; EC1.1.99.11), as enzyme, was dropped so as to cover the CMC layer and dried, to form a CMC-fructose dehydrogenase layer 7. In this CMC-fructose dehydrogenase layer 7, the CMC layer and the fructose dehydrogenase layer were mixed only by a thickness of several microns on the interface therebetween, namely, both layers were not completely mixed.

An ethanol solution including 0.5 wt % of polyvinylpyrrolidone (hereinafter called the PVP), as hydrophilic polymer, was dropped so as to completely cover the CMC-fructose dehydrogenase layer 7 and dried, to form a PVP layer 8.

When fruit juice including solid elements such as sarcocarp is used as a sample liquid, the solid elements are stopped by the PVP layer 8 provided on the CMC-fructose dehydrogenase layer 7, resulting in the prevention of the solid elements from being adsorbed to the surface of the electrode system 14. As a result, the response function of the sensor is prevented from being deteriorated. Furthermore, since the PVP layer 8 separates the fructose dehydrogenase contained in the CMC-fructose dehydrogenase layer 7 from potassium ferricyanide described below, the conservative and stable properties of the sensor can be remarkably improved.

Dispersing liquid, with crystals of potassium ferricyanide (the particle diameter: 0.5–4 $\mu$m), that is, electron acceptors, dispersed in a toluene solution including 0.5 wt % of lecithin as a dispersing agent was dropped and dried at room temperature, to form a potassium ferricyanide-lecithin layer 9 on the PVP layer 8.

Thus the reaction layer 15 comprising the CMC-fructose dehydrogenase layer 7, the PVP layer 8 and the potassium ferricyanide-lecithin layer 9 was formed.

Then, 3 $\mu$l of a phosphate buffer solution (a mixture of 0.2M of $K_2HPO_4$ and 0.2M of $KH_2PO_4$, pH=4.5) was dropped on a portion between the reaction layer 15 and the tip portion of the insulating substrate corresponding to a sample supply port 21, and dried, to form a hydrogen ion concentration control layer 11 as shown in FIGS. 1 and 3.

The enzyme used in this fructose sensor, that is, fructose dehydrogenase, shows the highest activity when pH is 4.5 (at 37° C.). Since a fructose standard solution is almost neutral, when the standard solution reaches the hydrogen ion concentration control layer 11, the pH of the solution becomes 4.5, thereby making the enzyme activity the highest. Alternately, when the sample liquid is acid or alkaline, the pH of the liquid is adjusted to be approximately 4.5, when the liquid reaches the hydrogen ion concentration control layer 11. Therefore, in the liquid that has passed the hydrogen ion concentration control layer 11, the enzyme activity will become higher as compared with in the originally supplied sample liquid.

Furthermore, the enzyme in the reaction layer 15 is separated from the hydrogen ion concentration control layer 11 by forming the hydrogen ion concentration control layer 11 away from the reaction layer 15, thereby the preservative property of the sensor is improved.

After forming the base 10 including the reaction layer 15 and the hydrogen ion concentration control layer 11 in the above-described way, the base 10, the spacer 20 and the cover 30 were laminated to be adhered as shown in FIGS. 2 and 3 with dashed lines. A reservoir for a sample liquid was formed as a space defined by the base 10, the wall of a groove 22 of the spacer 20 and the cover 30. As a result the sample liquid supply port 21 was formed at one end of the reservoir. An air port 31 was formed on a portion of the cover 30 opposing to the other end of the reservoir.

A sample liquid is supplied into the reservoir and introduced toward the reaction layer 15 only by allowing the sample liquid to contact the sample supply port 21 formed at the tip of the sensor. Since the supply amount of the sample liquid depends upon the volume of the reservoir, prior quantification of the liquid is not necessary. Furthermore, evaporation of the sample liquid during the measurement can be minimized, resulting in a measurement with high accuracy.

The thus produced fructose sensor was supplied with 3 $\mu$l of a fructose standard solution as a sample liquid from the sample supply port 21. Two minutes after the supply, a pulse voltage of +0.5 V on the basis of the voltage at the counter electrode 5 was applied to the working electrode 4. Then the anodic current value of five seconds after the application was measured.

When the sample liquid having obtained the desired pH after passing the hydrogen ion concentration control layer 11 reaches the reaction layer 15, the potassium ferricyanide-lecithin layer 9, the PVP layer 8 and the CMC-fructose dehydrogenase layer 7 are dissolved into the sample liquid successively in this order. The fructose contained in the sample liquid is oxidized by fructose dehydrogenase, and at this point the potassium ferricyanide is reduced to potassium ferrocyanide by shifted electrons. Then, an oxidation current corresponding to the concentration of the generated potassium ferrocyanide is caused by the application of the above pulse voltage. The current value corresponds to the concentration of the substrate, that is, fructose in this case.

Figure 4:
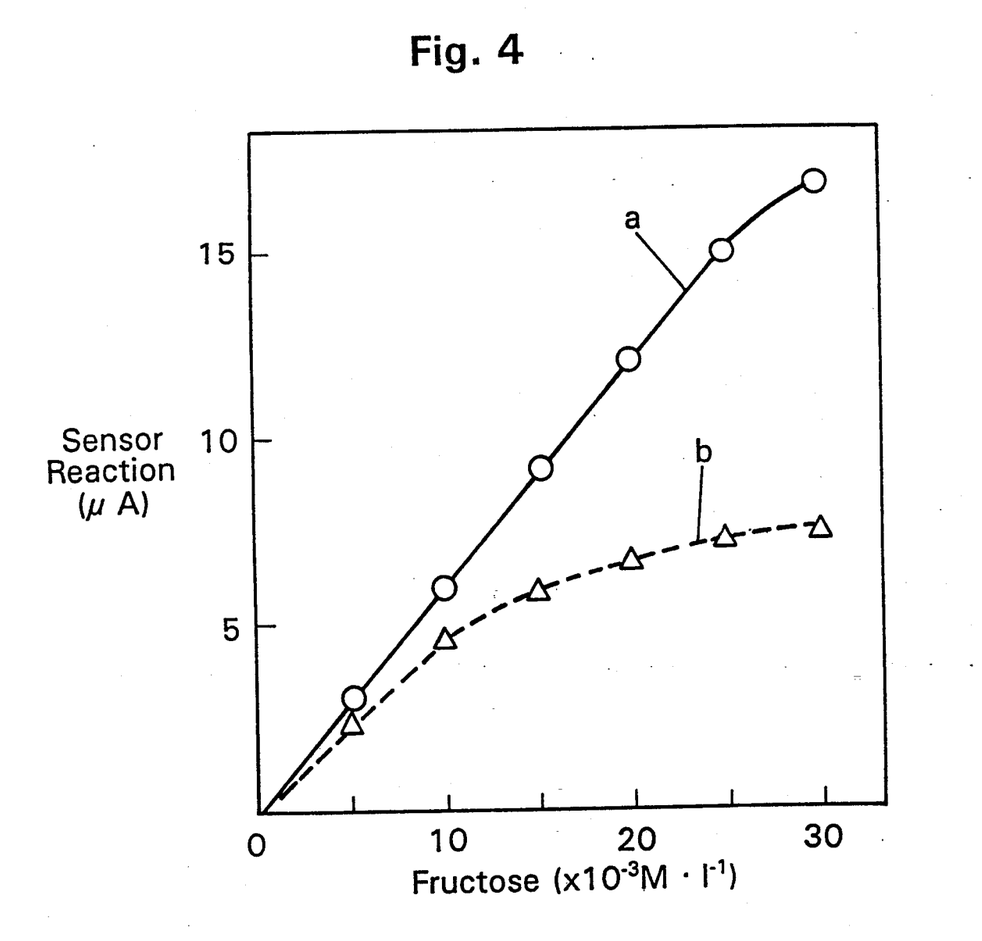
FIG. 4 is a diagram showing the response characteristics of the fructose sensor.

FIG. 4 shows the response property measured two minutes after the supply of the sample liquid by using the fructose sensor of this example. In the graph, the curve a shows responses of the fructose sensor of this example. The curve b shows responses of a comparative fructose sensor, in which the hydrogen ion concentration control layer 11 is removed from the base 10 of the fructose sensor, obtained in the same way as in this example.

As is evident from FIG. 4, in the fructose sensor of this example, the relation between the fructose concentration and the sensor response corresponded proportionally up to 25 mM of fructose, the substrate. On the other hand, in the fructose sensor without a hydrogen ion concentration control layer, the fructose concentration corresponded to the sensor response only up to 10 mM of fructose.

In FIG. 4, in the range where the corresponding relation between the fructose concentration and the sensor response is shown as a straight line, the response current value obtained by the fructose sensor of this example was larger by about 20% then that of the comparative fructose sensor without the hydrogen ion concentration control layer 11.

This example shows that a biosensor with a wide measuring range and a high sensitivity can be obtained by providing the hydrogen ion concentration control layer 11 on the base 10.

Furthermore, in the fructose sensor of this example, when the measuring time was set to be one minute, the relation that can be shown as a straight line was obtained up to 15 mM of fructose. The response repeatability of the sensor was also excellent. For example, the coefficient of variation (the CV value) in using thirty sensors as to the same sample liquid was 7% or less.

EXAMPLE 2

An electrode system 14 comprising a working electrode 4 and a counter electrode 5 as shown in FIG. 1 was formed on an insulating substrate 1 made from polyethylene terephthalate by means of screen printing in the same manner as in Example 1, and was ground and heat treated. A mixed aqueous solution including 0.5 wt % of CMC, fructose dehydrogenase and potassium ferricyanide was dropped on the electrode system 14 and was dried for 10 minutes in a warm-air dried at 40° C., to form a reaction layer 15.

The production procedure of a biosensor can be simplified by forming the reaction layer 15 by dropping and drying a mixed solution of hydrophilic polymer, enzyme and electron acceptors on the electrode system 14 in the above way.

Then, 3 $\mu$l of a McIlvaine buffer solution (a mixture of 0.1M of citric acid and 0.2M of disodium phosphate, pH=4.5) was dropped on a portion between the reaction layer 15 and a tip portion of the insulating substrate 1 corresponding to a sample supply port 21 of the sensor, and was dried to form a hydrogen ion concentration control layer 11. The thus obtained base 10, a spacer 20 and a cover 30 were laminated to be adhered as in Example 1 as shown in FIGS. 2 and 3 with dashed lines.

Three $\mu$l of a fructose standard solution was supplied to the thus obtained fructose sensor from the sample supply port 21. Two minutes after the supply, a pulse voltage of ±0.5 V on the basis of the voltage of the counter electrode 5 was applied to the working electrode 4. The anodic current value 5 seconds after the application was measured, resulting in obtaining a response current value corresponding to the fructose concentration in the sample liquid. Alternately, the sample liquid was supplied in the same manner and the voltage was applied after 90 seconds. The obtained response current was almost the same as that obtained after 2 minutes. Moreover, the coefficient of variation measured in using 30 sensors as to the same sample liquid was 5% or less. Thus, the repeatability was also excellent.

In the fructose sensor of this example, the fructose dehydrogenase mixed with potassium ferricyanide exists in the reaction layer 15. Therefore, both the fructose dehydrogenase and the potassium ferricyanide are easily dissolved into the sample liquid rapidly and uniformly. This rapid reaction in the mixture reduces the time required for measuring and makes the response current constant.

The response current obtained by the fructose sensor of this example was larger by about 20% than that of the comparative fructose sensor without a hydrogen ion concentration control layer as was used in Example 1.

EXAMPLE 3

An electrode system 14 comprising a working electrode 4 and a counter electrode 5 as shown in FIG. 1 was formed on an insulating substrate 1 made from polyethylene terephthalate by means of screen printing in the same manner as in Example 1, and was ground and heat treated. Then, 3 $\mu$l of a phosphate buffer solution (a mixture of 0.2M of $K_2HPO_4$ and 0.2M of $KH_2PO_4$, pH=4.5) including potassium ferricyanide was dropped on a portion between the electrode system 14 and the tip portion of the insulating substrate corresponding to a sample supply port 21, and was dried at 100° C. for 5 minutes by heating as shown in FIGS. 1 and 3, to form a hydrogen ion concentration control layer 11 including potassium ferricyanide.

The time required for drying the hydrogen ion concentration control layer 11 depends upon the temperature at which the layer is heated. Therefore, the crystal diameter of the potassium ferricyanide contained in the hydrogen ion concentration control layer 11 can be controlled by the heat treatment condition. The crystal diameter of the potassium ferricyanide becomes smaller when the drying time is shorter, resulting in increasing the solubility speed into the sample liquid. Thus the response speed of the sensor can be increased. On the other hand, when the potassium ferricyanide coexists with the enzyme in the reaction layer 15, the enzyme activity is reduced by heating the reaction layer 15 at a high temperature. Therefore, the heating temperature of the layer 15 can not be set freely.

Furthermore, as in the present example, when the enzyme in the reaction layer 15 is separated from the potassium ferricyanide by containing the potassium ferricyanide in the hydrogen ion concentration control layer 11, the shelf life of the sensor can be remarkably increased.

Then, a mixed aqueous solution including 0.5 wt % of CMC and fructose dehydrogenase was dropped on the electrode system 14, and was dried in a warm-air drier at 40° C. for 10 minutes, to form the reaction layer 15. The thus formed base 10, a spacer 20 and a cover 30 were laminated to form a fructose sensor.

The fructose sensor produced in the above way was supplied with 3 $\mu$l of a fructose standard solution from the sample supply port 21. The sensor response was measured 2 minutes after the supply in the same manner as in Example 1. As a result, the obtained current value corresponded to the fructose concentration in the sample liquid. Alternately, when the voltage was applied 90 seconds after supplying the sample liquid as described above, the response current value was approximately the same as that obtained after 2 minutes. This is because the potassium ferricyanide in the sample liquid was rapidly dissolved due to the smaller crystal diameters of the potassium ferricyanide (0.05–0.3 $\mu$m).

The response current obtained by the fructose sensor of this example was larger by about 20% than that of the comparative fructose sensor without a hydrogen ion concentration control layer 11 as was in Example 1.

EXAMPLE 4

A sucrose sensor will now be described as another example of a biosensor.

An electrode system 14 comprising a working electrode 4 and a counter electrode 5 as shown in FIG. 1 was formed on an insulating substrate 1 made from polyethylene terephthalate, and was ground and heat treated. Then, an aqueous solution including 0.5 wt % of CMC was dropped on the electrode system 14 and was dried to form a CMC layer. Then a mixed aqueous solution including 0.5 wt % of CMC, invertase (EC 3.2.1.26), mutarotase (EC5.1.3.3), glucose oxidase (EC1.1.3.4) and potassium ferricyanide was dropped on the CMC layer and was dried in a warm-air drier at 40° C. for 10 minutes to form a reaction layer 15.

Then a phosphate buffer solution (pH=7.4) was dropped on a portion between the reaction layer 15 and the tip portion of the insulating substrate 1 corresponding to a sample supply port 21, then was dried to form a hydrogen ion concentration control layer 11. The thus obtained base 10, a spacer 20 and a cover 30 were laminated to form a sucrose sensor.

Three μl of a sucrose standard solution was supplied to the sucrose sensor from the sample supply port 21. Two minutes after the supply, a pulse voltage of ±0.5 V on the basis of the voltage of the counter electrode 5 was applied to the working electrode 4. Then the anodic current value after 5 seconds was measured. As a result, the obtained response current value corresponded to the sucrose concentration in the sample liquid.

EXAMPLE 5

Figure 5:
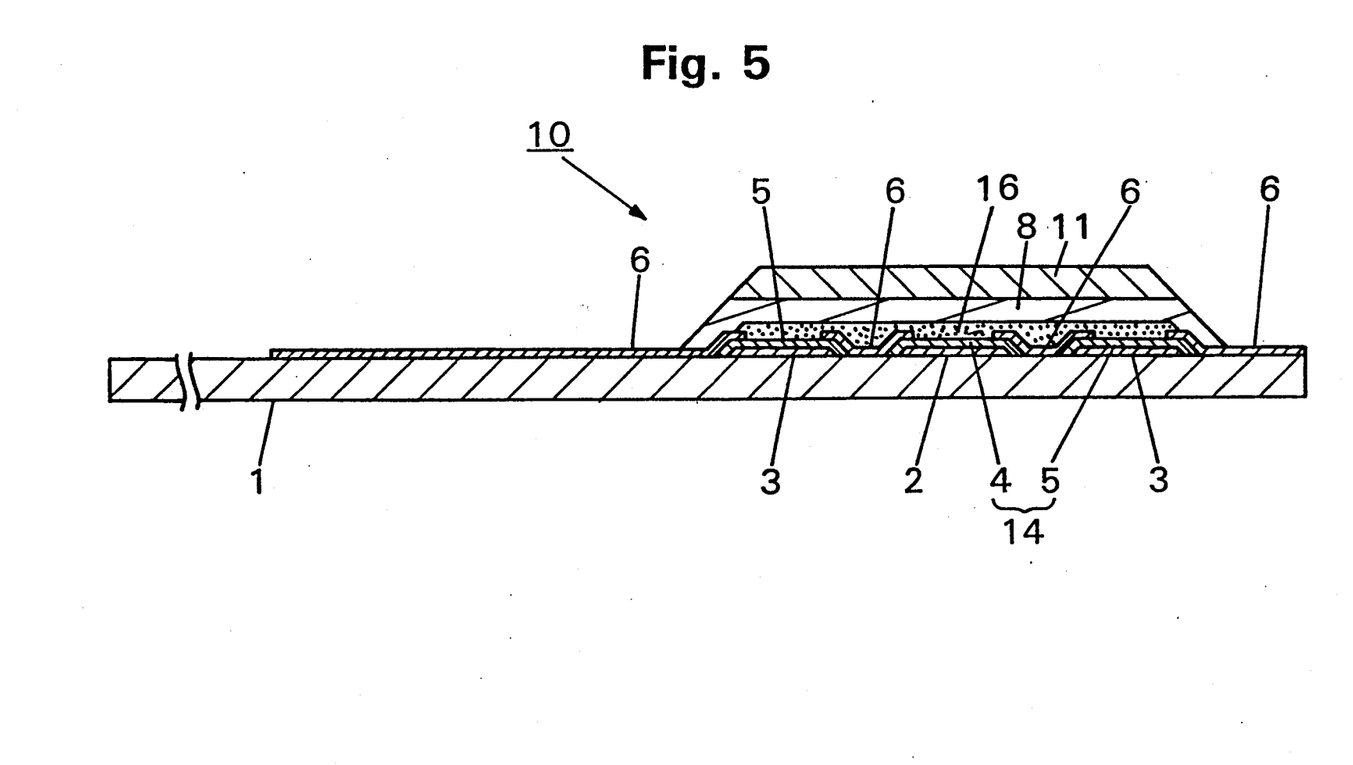
FIG. 5 is a sectional view of a base of a fructose sensor according to another example of the present invention.

An electrode system 14 comprising a working electrode 4 and a counter electrode 5 was formed on an insulating substrate 1 made from polyethylene terephthalate by means of screen printing as shown in FIG. 5, and was ground and heat treated. A mixed aqueous solution including 0.5 wt % of CMC, fructose dehydrogenase and potassium ferricyanide was dropped on the electrode system 14, and was dried in a warm-air dried at 40° C. for 10 minutes to form a CMC-fructose dehydrogenase-potassium ferricyanide layer 16.

Then, an ethanol solution including 0.5 wt % of PVP as hydrophilic polymer was dropped so as to cover the entire CMC-fructose dehydrogenase-potassium ferricyanide layer 16, and was dried to form a PVP layer 8. 3 μl of a McIlvaine buffer solution (a mixture of 0.1M of citric acid and 0.2M of disodium phosphate, pH=4.5) was dropped on the PVP layer 8, and was dried to form a hydrogen ion concentration control layer 11.

In the example, the hydrogen ion concentration control layer 11 and the PVP layer 8 are mixed only by a thickness of several microns on the interface therebetween since PVP is hydrophilic polymer. Therefore, the CMC-fructose dehydrogenase-potassium ferricyanide layer 16 is separated from the hydrogen ion concentration control layer 11 by the PVP layer 8. In this example, a reaction layer 15 comprises the CMC-fructose dehydrogenase-potassium ferricyanide layer 16.

Thus, the time required for solution of the reaction layer 15 into the sample liquid after the hydrogen ion concentration control layer 11 is dissolved, because the hydrogen ion concentration control layer 11 is formed on the reaction layer 15, thereby reducing the time required for the sensor response.

Furthermore, in the fructose dehydrogenase used in this example as enzyme, the pH for allowing the enzyme activity to be the highest is different from the pH for providing a high conservative stability of the sensor. Therefore, in the conventional biosensor as shown in FIG. 7, the shelf life of the sensor is deteriorated because the sensor is under a pH condition which is different from that providing the fructose dehydrogenase with a high stability when the biosensor absorbs moisture.

The biosensor of this example can overcome the above-mentioned disadvantage because the CMC-fructose dehydrogenase-potassium ferricyanide layer 16 can be separated from the hydrogen ion concentration control layer 11 by the PVP layer 8.

Figure 6:
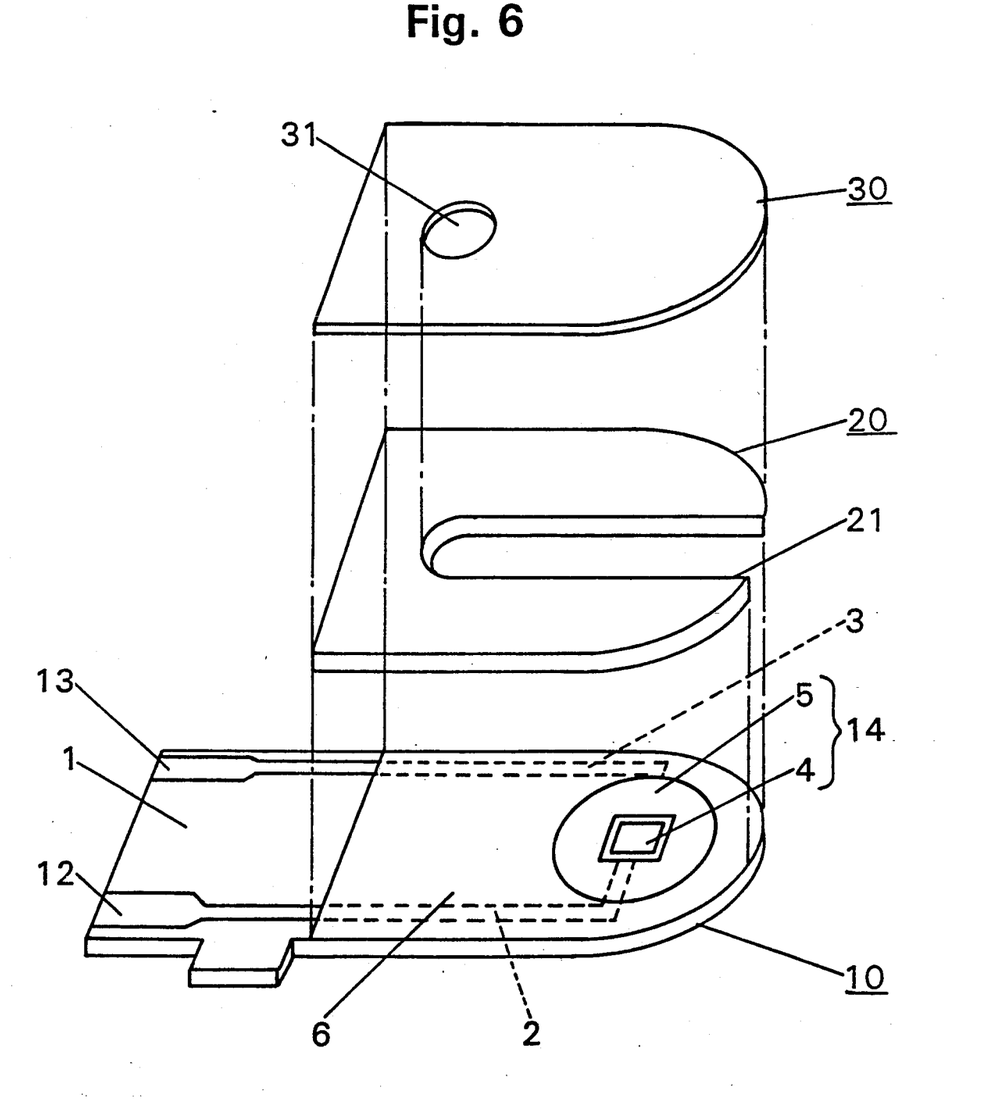
FIG. 6 is an exploded perspective view of the fructose sensor of FIG. 5.

Moreover, in the biosensor of this example, it is not necessary to distinguish a sample supply port 21 provided to the sensor from an air port 31. Therefore, the sample supply port 21 can be used as an air port, from which it is possible to supply the sample liquid.

After forming the base 10 including the reaction layer 15 and the hydrogen ion concentration control layer 11 in the above-mentioned manner, the base 10, a spacer 20 and a cover 30 were laminated so as to be adhered as shown in FIG. 6 with dashed lines.

The thus obtained fructose sensor was supplied with 3 μl of a fructose standard solution as a sample liquid from the sample supply port 21, and the sensor response was measured in the same manner as in Example 1. The obtained result was a proportional linear relation up to 25 mM of fructose. Furthermore, the coefficient of variation (the CV value) obtained in using 30 sensors was 6% or less. Thus the repeatability was excellent.

EXAMPLE 6

An electrode system 14 comprising a working electrode 4 and counter electrode 5 was formed on an insulating substrate 1 made from polyethylene terephthalate by means of screen printing in the same manner as in Example 1, and was ground and heat treated. An aqueous solution including potassium ferricyanide and CMC was dropped on the electrode system 14 and dried by heating, to form a layer including CMC and potassium ferricyanide.

The time required for drying the layer depends upon the heating temperature. Therefore, the crystal diameter of the potassium ferricyanide contained in the layer can be controlled by the heat treatment condition. A shorter drying time makes the crystal diameter of the potassium ferricyanide smaller, therefore increasing solubility speed into the sample liquid. In this way, the response speed can be increased. On the other hand, when potassium ferricyanide coexists with enzyme in the reaction layer, the heating temperature can not be freely set, because the enzyme activity is reduced by heating at a high temperature.

Then, an ethanol solution including 0.5 wt % of PVP was dropped so as to cover the entire layer including potassium ferricyanide and CMC, and was dried to form a PVP layer. Furthermore, a fructose dehydrogenase solution was dropped on the PVP layer, and was dried to form a fructose dehydrogenase layer.

Then, an ethanol solution including 0.5 wt % of hydroxyethyl cellulose so as to cover the entire fructose dehydrogenase layer, and was dried to form a hydroxyethyl cellulose layer. Furthermore, a phosphate buffer solution (pH=4.5) was dropped on the hydroxyethyl cellulose layer, and was dried to form a hydrogen ion concentration control layer 11. The thus obtained base 10, a spacer 20 and a cover 30 were laminated in the same manner as in Example 1 to form a fructose sensor.

PVP and hydroxyethyl cellulose are hydrophilic polymer. Therefore, when an aqueous solution including fructose dehydrogenase is dropped on the PVP layer, the PVP layer and the fructose dehydrogenase layer are not completely mixed but only mixed by a thickness of several microns on the interface therebetween. Also when a phosphate buffer solution is dropped on the hydroxyethyl cellulose layer, the hydroxyethyl cellulose layer and the hydrogen ion concentration control layer are not completely mixed but only mixed by a thickness of several microns on the interface therebetween.

In this way, the CMC-potassium ferricyanide layer is separated from the fructose dehydrogenase layer and the hydrogen ion concentration control layer respectively.

The fructose sensor produced in the above method was supplied with 3 μl of a fructose standard solution from a sample supply port. The sensor response after 2 minutes obtained in the same manner as in Example 1 corresponded to the fructose concentration in the sample liquid. Alternately, when the voltage was applied 90 seconds after the supply, the response current was approximately the same as that obtained 2 minutes after. This is because potassium ferricyanide dissolved into the sample liquid more quickly due to the smaller crystal diameter of the potassium ferricyanide.

The response current values obtained by the fructose sensor of this example were larger by about 20% than those obtained by the comparative fructose sensor without a hydrogen ion concentration control layer 11, as was in Example 1.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A biosensor for quantifying a substrate contained in a sample liquid by reducing electron acceptors using electrons generated in a reaction of the substrate to enzyme and then by measuring the reduced amount of the electron acceptors electrochemically, the biosensor comprising:

an electrical insulating substrate, an electrode system including at least a working electrode and a counter electrode which are formed on the insulating substrate, a reaction layer including the enzyme provided on the electrode system, and a hydrogen ion concentration control layer;

the reaction layer being in contact with the electrode system.

2. A biosensor according to claim 1, wherein the reaction layer further includes hydrophilic polymer and electron acceptors.

3. A biosensor according to claim 1, wherein the reaction layer further includes hydrophilic polymer and the hydrogen ion concentration control layer includes electron acceptors.

4. A biosensor according to claim 2, wherein the reaction layer is formed by laminating a first layer including hydrophilic polymer and enzyme, a second layer including hydrophilic polymer and a third layer including electron acceptors in this order.

5. A biosensor according to claim 1, wherein the hydrogen ion concentration control layer is provided on the electrode system.

6. A biosensor according to claim 5, wherein the reaction layer further includes hydrophilic polymer and electron acceptors, and a hydrophilic polymer layer is provided between the reaction layer and the hydrogen ion concentration control layer.

7. A biosensor according to claim 5, wherein the reaction layer comprises a first layer including hydrophilic polymer and electron acceptors and a second layer including enzyme laminated on the first layer, and the hydrogen ion concentration control layer is provided on the second layer.

8. A biosensor according to claim 1, wherein the electrode system is mainly formed from carbon.

9. A biosensor according to claim 1, wherein the hydrogen ion concentration control layer includes buffering salt selected from the group consisting of potassium biphosphate-dipotassium phosphate, potassium biphosphate-disodium phosphate, citric acid-disodium phosphate, citric acid-trisodium citrate, potassium bicitrate-sodium hydroxide and maleic acid monosodium salt-sodium hydroxide.

10. A biosensor according to claim 1, wherein the hydrophilic polymer is selected from the group consisting of carboximethyl cellulose, polyvinyl pyrrolidone, hydroxyethyl cellulose, hydroxy proryl cellulose, methyl cellulose, ethyl cellulose, ethyl hydroxyethyl cellulose, carboxy methyl ethyl cellulose, polyvinyl alcohol and gelatin.

11. A biosensor according to claim 1, wherein the enzyme is selected from the group consisting of fructose dehydrogenase, invertase, mutarotase, glucose oxidase, alcohol oxidase, lactate oxidase, lactate dehydrogenase, cholesterol oxidase, xanthine oxidase and amino acid oxidase.

12. A biosensor according to claim 1, wherein the electron acceptor is selected from the group consisting of potassium ferricyanide, p-benzoquinone, phenazinemethosulfate and ferrocene.

13. A method for producing a biosensor for quantifying a substrate contained in a sample liquid by reducing electron acceptors using electrons generated in a reaction of the substrate to enzyme and then by measuring the reduced amount of the electron acceptors electrochemically, the method comprising the steps of:

firstly, providing an electrode system including at least a working electrode and a counter electrode on an electrical insulating substrate;

secondly, forming a hydrogen ion concentration control layer including electron acceptors on the insulating substrate; and finally, forming a reaction layer including hydrophilic polymer and enzyme on the electrode system.

* * * * *